United States Patent
Steele et al.

(10) Patent No.: US 11,964,071 B2
(45) Date of Patent: Apr. 23, 2024

(54) ELECTROACTIVE BIOADHESIVE COMPOSITIONS

(71) Applicants: NANYANG TECHNOLOGICAL UNIVERSITY, Singapore (SG); YISSUM RESEARCH DEVELOPMENT COMPANY OF THE HEBREW UNIVERSITY OF JERUSALEM LTD, Jerusalem (IL)

(72) Inventors: Terry W. J. Steele, Singapore (SG); Daniel Mandler, Jerusalem (IL)

(73) Assignees: NANYANG TECHNOLOGICAL UNIVERSITY, Singapore (SG); YISSUM RESEARCH DEVELOPMENT COMPANY OF THE HEBREW UNIVERSITY OF JERUSALEM LTD, Jerusalem (IL)

( * ) Notice: Subject to any disclaimer, the term of this patent is extended or adjusted under 35 U.S.C. 154(b) by 0 days.

(21) Appl. No.: 17/831,392

(22) Filed: Jun. 2, 2022

(65) Prior Publication Data
US 2022/0296771 A1    Sep. 22, 2022

Related U.S. Application Data

(62) Division of application No. 15/111,567, filed as application No. PCT/SG2015/000009 on Jan. 14, 2015, now Pat. No. 11,357,884.

(60) Provisional application No. 61/927,186, filed on Jan. 14, 2014.

(51) Int. Cl.
| | |
|---|---|
| *A61B 17/00* | (2006.01) |
| *A61L 24/00* | (2006.01) |
| *A61L 24/04* | (2006.01) |
| *A61L 24/08* | (2006.01) |
| *H01B 1/12* | (2006.01) |

(52) U.S. Cl.
CPC ...... *A61L 24/001* (2013.01); *A61B 17/00491* (2013.01); *A61L 24/0015* (2013.01); *A61L 24/0031* (2013.01); *A61L 24/04* (2013.01); *A61L 24/08* (2013.01); *H01B 1/124* (2013.01); *A61B 2017/005* (2013.01); *A61L 2300/216* (2013.01); *A61L 2400/00* (2013.01)

(58) Field of Classification Search
CPC ............ A61L 24/001; A61L 24/0015; A61L 24/0031; A61L 24/04; A61L 24/08; A61L 2300/216; A61L 2400/00; A61B 17/00491; A61B 2017/005; H01B 1/124
See application file for complete search history.

(56) References Cited

U.S. PATENT DOCUMENTS

| | | | |
|---|---|---|---|
| 4,284,705 | A | 8/1981 | Phlipot et al. |
| 5,380,923 | A | 1/1995 | Wright et al. |
| 6,187,945 | B1 | 2/2001 | Yasuda et al. |
| 2009/0286308 | A1 | 11/2009 | Berthelot et al. |
| 2010/0211151 | A1 | 8/2010 | Scott-Carnell et al. |

FOREIGN PATENT DOCUMENTS

| | | | |
|---|---|---|---|
| CA | 2 255 493 | A1 | 6/2000 |
| EP | 0 330 344 | A2 | 8/1989 |
| EP | 2 341 089 | A1 | 7/2011 |
| EP | 2 674 173 | A1 | 12/2013 |
| JP | 2007-254307 | A | 10/2007 |
| WO | 2006/049791 | A1 | 5/2006 |
| WO | 2006/049792 | A1 | 5/2006 |
| WO | 2008/023170 | A1 | 2/2008 |
| WO | 2008/121033 | A1 | 10/2008 |
| WO | 2009/097152 | A1 | 8/2009 |
| WO | 2010/100410 | A1 | 9/2010 |
| WO | 2010/100413 | A2 | 9/2010 |

OTHER PUBLICATIONS

Written Opinion dated Apr. 21, 2015, from corresponding International Application No. PCT/SG2015/000009, 9 pages.
International Search Report, dated Apr. 21, 2015, from corresponding International Application No. PCT/SG2015/000009, 4 pages.
Jones et al., "Direct Peptide Bioconjugation/PEGylation at Tyrosine with Linear and Branched Polymeric Diazonium Salts," *J. Am. Chem. Soc.* 134(17):7406-7413, 2012.
Murphy et al., "Modification of Silk Fibroin Using Diazonium Coupling Chemistry and the Effects on hMSC Proliferation and Differentiation," *Biomaterials* 29(19):2829-2838, Jul. 2008.

*Primary Examiner* — Alma Pipic
(74) *Attorney, Agent, or Firm* — Seed IP Law Group LLP

(57) ABSTRACT

Electrochemically initiated bioadhesive compositions comprising biocompatible polymers containing derivatives of diazonium, arylsulfonium, or diaryliodonium in general, and to their use in tissue fixation, in particular.

13 Claims, 3 Drawing Sheets

1

ELECTROACTIVE BIOADHESIVE COMPOSITIONS

FIELD OF THE INVENTION

The present invention relates to electrochemically initiated bioadhesive compositions comprising biocompatible polymers containing derivatives of diazonium, arylsulfonium, or diaryliodonium in general, and to their use in tissue fixation, in particular.

BACKGROUND OF THE INVENTION

Current methods of tissue fixation leave much to be desired; essentially relying on technologies developed from the clothing and carpentry industries. Screws, pins, wires, sutures, and buttress plates, are examples of bone and soft tissue fixation implants. These devices have many disadvantages, including the need for subsequent operations for removal and interference with mobility and growth impediments in youths. They also have high rates of complications, such as infection and tissue inflammation.

With the market value of tissue fixation devices estimated at approximately four billion dollars, many attempts have been made to improve upon these implants. Resorbable implants have made inroads in addressing some of the issues above, however they still have problems with the destructive nature of the mechanical fixation. For example, the trauma induced by resorbable suturing on intestinal tissue upregulates enzymes that breakdown collagen (the structural component) for up to 4 days post-procedure—weakening the intestine tissue and raising the probabilities of tears and intestinal leakages—but it's still the standard operating procedure for intestinal anastomoses. Intestinal anastomoses are typically performed for treatment of colorectal cancer.

'Gluing' soft-tissues and biomaterials together is far more convenient than sutures and conventional tissue fixation, but development of a suitable bioadhesive has yet to be fully realized. Bioadhesive 'glues' are a significant engineering hurdle in numerous fields including wound closures, implantable electronics, meshes for abdominal surgeries, and tissue engineering transplants. Medical grade cyanoacrylates, for example Dermabond® and Super Glue®, and fibrin tissue adhesives, for example Tisseal® and Evicel®, are currently the only commercially available and FDA approved bioadhesives that have addressed soft tissue fixation. Unfortunately, they trade adhesive strength for biocompatibility or vice versa. Cyanoacrylates typically have strong tissue adhesion, but are relatively inflexible. Their brittleness, combined with local tissue toxicity and incapability of local drug delivery limits them to skin and other topical adhesions. Fibrin-based tissue adhesives have many shortcomings as well. Their bioadhesion is 'hydrogel' weak, has potential neurotoxicity complications and serious religious concerns due to the predominantly human (or bovine) fibrinogen and thrombin sources. Due to their weak mechanical properties, fibrin tissues adhesives are best suited for control of bleeding.

WO 2010/100410 and WO 2010/100413 disclose functionalized diazo derivatives, including diazopyruvate, and their use for producing a chemically-bound three-dimensional network on or within a substrate.

WO 2009/097152 relates to calcium-reactive amines and acrylic or methacrylic ester monomers adhesives, and use thereof for adhering dental and medical biomaterials to hard tissues via a molecular bridge formed from to hard tissues such as enamel, dentin, and bone.

JP 2007254307A describes a dental adhesive that comprises of a polymerizable monomer including an acidic group-containing polymerizable monomer, water and a polymerization initiator comprising a photo acid generator, an oxidation type photoradical generator. The photo acid generator is preferably a diaryl iodonium salt-based compound, but the activation of the adhesive is by photoactivation.

WO 2008/023170 describes a group of diazo compounds used as aryl carbene precursors for use in the process of producing a substrate having an adhesive surface, which allows the substrate to adhere to other materials to be tailored.

WO 2008/121033 provides an adhesive for facilitating the adhesion between an electroactive polymer and a substrate, wherein the adhesive consists of a platinum or an alloy comprising platinum.

EP 0330344 relates to use of crosslinked collagen as a bioadhesive for sutureless closures of the skin and eye or as a superhydrated material for contact lenses, moist bandage contact lens, lens or corneal implant material, or as a drug delivery agent. According to EP 0330344, collagen, which is an example of amino-acid containing polymers, is cross-linked into a highly molecularly crosslinked product upon photoactivation with photoactive crosslinking reagents, such as diazo or azide derivatives.

Failure of soft tissue bioadhesives to address local tissue fixation and biocompatibility has prompted urgent need for a new bioadhesive that allows biomaterials to be adhered onto soft tissues while maintaining a high level of biocompatibility and adhesive strength.

SUMMARY OF THE INVENTION

Various embodiments of the invention provide electrochemically activated or electroactive bioadhesive compositions containing diazonium, arylsulfonium, or diaryliodonium and the respective derivatives, and their use in tissue fixation.

In one embodiment, an electroactive polymer comprises a biocompatible polymer comprising a single strand of repeating units and up to 5,000 electroactive groups covalently attached to said strand, wherein said electroactive polymer has a molecular weight of up to 3 million Daltons, and wherein said electroactive groups are derivatives of diazonium salts, derivatives of arylsulfonium salts, derivatives of diaryliodonium salts, or combination thereof.

In particular embodiments, said biocompatible polymer can be any bioresorbable polymer that has been FDA-approved as a medical device selected from the group consisting of polyethylene glycol (PEG), PEG fatty acid esters, poly-L-lactic acid (PLLA), poly(lactide-co-glycolide) (PLGA), poly caprolactone (PCL), polyvinyl pyrrolidone (PVP), polyvinyl alcohol (PVA), collagen, chitosan, hydroxy propyl cellulose, polyamides, polyglycerol esters of fatty acids, polysaccharides, polyesters, and combinations thereof. The polysaccharide is selected from the group consisting of dextran, chitosan, heparin, hyaluronic acid, alginates, starch, glycogen, amylose, amylopectin, cellulose, xylan, and numerous other natural and synthetic polysaccharides.

In a further embodiment, the electroactive diazonium derivative is a compound of the following formula:

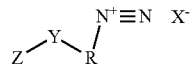

wherein
X is an inorganic or organic anion selected from the group consisting of anion of $F^-$, $Cl^-$, $Br^-$, $I^-$, $BF_4^-$, $BF_3$, $ZnCl_2$, $HSO_4^-$, $PF_6^-$, $HgBr_2$, $HgBr_2Cl_2$, $NO_3^-$, nonafluoro-1-butanesulfonate, trifluoromethanesulfonate, dimethoxy-2-anthracenesulfonate, and methylbenzenesulfonate;

R is a bond or 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group;

Y is a bond or saturated and unsaturated $C_1$-$C_{500}$ straight-chain or branched alkyl, alkenyl or alkynyl group, wherein said chain may optionally incorporate at least one hetero atom, and may also comprise at least one substituent; and Z is any suitable functional group selected from the group consisting of halogen, amino, cyano, hydroxy, aldehyde, alkoxycarbonyl, N-amide, N-hydroxysuccinimide ester, maleimide, and thiol.

In specific embodiments, the electroactive diazonium derivative can be selected from the list of:

4-(dimethylamino)-benzene-diazonium salt;
2-chloro-benzene-diazonium salt;
1-naphthalene-diazonium salt;
4-anilino-benzene-diazonium salt;
3,5-dichloro-benzene-diazonium salt;
1-pyrene-diazonium salt;
4-Methoxy-benzene-diazonium salt;
4-bromo-benzene-diazonium salt;
4-formyl-benzene-diazonium salt;
4-Nitro-benzene-diazonium salt;
Fast Red TR salt;
Variamine blue B salt;
4-[ethyl(2-hydroxyethyl)amino]-benzene-diazonium salt;
4-(diethylamino)-2-methyl-benzene-diazonium salt;
4-(ethylamino)-3-methyl-benzene-diazonium salt;
5-chloro-2-methoxy-benzene-diazonium salt;
3-methyl-4-nitro-benzene-diazonium salt;
bis[4-(diethylamino)-2-methyl-benzene-diazonium] salt;
2,4-dichloro-benzene-diazonium salt;
2-methoxy-4-nitro-benzene-diazonium salt;
2-chloro-4-nitro-benzene-diazonium 2-naphthalenesulfonate;
2,5-diethoxy-4-[(4-methylphenyl)sulfanyl]benzenediazonium salt;
Fast Blue B salt;
9H-fluorene-2-diazonium salt;
9,10-dioxo-9,10-dihydro-1-anthracenediazonium salt; and
2-Methoxy-4-morpholinobenzenediazonium salt.

In a further embodiment, the electroactive diaryliodonium derivative is a compound of the following formula:

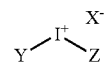

Wherein
X is an inorganic or organic anion selected from the group consisting of anion of $F^-$, $Cl^-$, $Br^-$, $I^-$, $BF_4^-$, $BF_3$, $ZnCl_2$, $HSO_4^-$, $PF_6^-$, $HgBr_2$, $HgBr_2Cl_2$, $NO_3^-$, nonafluoro-1-butanesulfonate, trifluoromethanesulfonate, dimethoxy-2-anthracenesulfonate, and methylbenzenesulfonate;

Y is a 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group; and Z is a 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group;

In specific embodiments, the electroactive diaryliodonium derivative can be selected from the list of:

Diphenyliodonium iodide salt;
bis(4-methoxyphenyl)iodonium salt;
bis(4-methylphenyl)iodonium salt;
bis(4-tert-butylphenyl)iodonium salt;
4-(phenyliodonio)benzoate salt;
bis(4-fluorophenyl)iodonium salt;
bis(4-bromophenyl)iodonium salt;
bis(4-tert-butylphenyl)iodonium salt;
mesityl(4-methylphenyl)iodonium salt;
2-(phenyliodonio)benzoate salt;
2-(phenyliodonio)benzoate;
(4-nitrophenyl)(phenyl)iodonium;
phenyl[3-(trifluoromethyl)phenyl]iodonium salt;
(3-bromophenyl)(mesityl)iodonium salt;
(2-bromophenyl)(mesityl)iodonium salt;
mesityl[3-(trifluoromethyl)phenyl]iodonium salt;
mesityl(4-nitrophenyl)iodonium salt;
Diphenyleneiodonium salt; and
3,7-dinitrodibenziodolium salt.

In a further embodiment, the electroactive arylsulfonium derivative is a compound of the following formula:

Wherein

X is an inorganic or organic anion selected from the group consisting of anion of $F^-$, $Cl^-$, $Br^-$, $I^-$, $BF_4^-$, $BF_3$, $ZnCl_2$, $HSO_4^-$, $PF_6^-$, $HgBr_2$, $HgBr_2Cl_2$, $NO_3^-$, nonafluoro-1-butanesulfonate, trifluoromethanesulfonate, dimethoxy-2-anthracenesulfonate, and methylbenzenesulfonate;

Y is a bond, $C_1$-$C_8$ straight-chain or branched alkyl group, or 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group;

Z is a bond, $C_1$-$C_8$ straight-chain or branched alkyl group, or 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group; and W is a bond, $C_1$-$C_8$ straight-chain or branched alkyl group, or 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group; wherein at least two of W, Y and Z are not a bond, $C_1$-$C_8$ straight-chain or branched alkyl group.

In specific embodiments, the electroactive arylsulfonium derivative can be selected from the list of:

Triphenylsulfonium salt;
diphenyl[4-(phenylsulfanyl)phenyl]sulfonium salt;
(4-fluorophenyl)(diphenyl)sulfonium salt;
tris(4-tert-butylphenyl)sulfonium salt;
tris(4-chlorophenyl)sulfonium salt;
(4-chlorophenyl)diphenylsulfonium salt;
tri-p-tolylsulfonium salt;
tris(4-methoxyphenyl)sulfonium salt;
(4-methoxyphenyl)diphenylsulfonium salt;
ethyl(4-methoxyphenyl)(phenyl)sulfonium salt;
(3-chloropropyl)diphenylsulfonium salt; and
(5-chloropentyl)diphenylsulfonium salt.

In another embodiment, an electroactive bioadhesive composition comprises the electroactive polymer of the present invention and suitable solvents, surfactants, stabilizers, fillers and other additives. The additives may be anti-inflammatory drugs, anti-proteases, antibiotics, and/or anti-restenosis compounds.

In yet further embodiment, the composition can be in a form of hydrogel, biocompatible film, patch or bondage. In addition, the composition may contain conductive particles or polymers of size less than 50 micron made of gold, iron, iron oxides, platinum, magnesium, graphene, carbon black, carbon nanotubes, polyacetylene, poly(3-alkyl-thiophene), polyaniline, polyisothianaphthalene, poly-(p-phenylene), poly-(p-phenylene vinylene), polypyrole, polythiophene, or combinations thereof. The composition is electrically conductive with conductivity greater than 0.01 siemen per centimeter.

In additional embodiment, the conductive particles can be coated with anionic or cationic coating comprising fatty acids, silica, polyethylene glycol, pluronics, poloxamers, polydopamine, polylysine or any suitable peptide.

In a general embodiment, the composition may be used in surgery, such as gastrointestinal surgery towards cancer removal, anastomoses procedures, such as blood vessel anastomoses wherein two tubes or lumens must be joined, tissue fixation, suture sealing and replacement, treatment of lung punctures, body lumen punctures or leaks, cerebrospinal fluid membrane damages, obesity treatments, and bowel obstructions.

In still another embodiment, a method for the preparation of the electroactive polymer of the present invention comprises the steps of:
(a) Preparing a solution of said biocompatible polymer having concentration of 0.1 to 100 mg/ml at pH 7.2;
(b) Dissolving said electroactive derivatives of diazonium, arylsulfonium, or diaryliodonium compound in a suitable organic solvent within the concentration range of 0.01 to 100 mM;
(c) Mixing and reacting the solution of said biocompatible polymer prepared in a) with the solution of the electroactive derivative prepared in b), in order to covalently attach the electroactive groups to the polymer strand; that is in the form of a thin film on a conductive material, i.e. the electrode.
(d) Purifying said polymer modified in c) on a Sephadex G-25 column or using other conventional purification and separation techniques in order to remove the unbound electroactive derivative molecules.

In yet another embodiment, method of tissue fixation comprises the steps of:
(a) Applying the electroactive bioadhesive composition of the present invention, being a hydrogel, film, patch or bondage, to a tissue to be fixed; and
(b) Applying a voltage potential to an electrode on which the electroactive polymer is placed, across the composition and tissue area with negative 10 to positive 10 Volts vs. a reference electrode that can be of any type such as Ag/AgCl or Ag wire or any other electrode that has a constant potential, which depends on the composition, in an electrolyte with a concentration of between 0.01 and 1 M.

In still further embodiment, voltage potential is between negative 5 to positive 5 Volts, such as negative 2 to positive 2 Volts, and time of voltage potential in both cases is less than 20 minutes. The potential can be applied also in a sweeping mode, i.e., by changing the potential under a fixed or changeable scan rate (in mV/s) and scanning one or several cycles.

Various embodiments of the invention may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The present invention will be understood and appreciated more fully from the following detailed description taken in conjunction with the appended figures. Various exemplary embodiments are well illustrated in the accompanying figures with the intent that these examples not be restrictive. It will be appreciated that for simplicity and clarity of the illustration, elements shown in the figures referenced below are schematic. Of the accompanying figures.

DETAILED DESCRIPTION OF THE INVENTION

Figure 1:
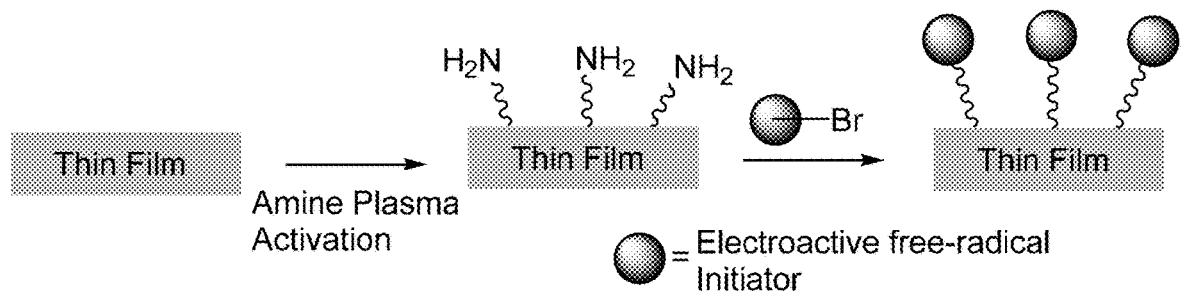
FIG. 1 is a synthetic route to thin films crosslinked with diazonium, arylsulfonium, or diaryliodonium derivatives used in the tissue fixation.

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

It should be noted that although a portion of the discussion may relate to electroactive bioadhesive materials, compositions and methods, the present invention is not limited in this regard, and embodiments of the present invention may be used in conjunction with various other biomaterials, compositions and methods of treatment. As such, some embodiments of the invention may be used, for example, in conjunction with use of various biocompatible films, patches or bondages and in various surgery procedures. Some embodiments of the invention may be used not necessarily in the context of in vivo treatment.

"Biocompatible" material is defined as a natural or synthetic material having low variability, high purity, and no detectable biological reactivity as determined by biocompatibility tests. "Biocompatible polymer" is a natural or synthetic polymer having low variability, high purity, and no detectable biological reactivity as determined by biocompatibility tests. "Bioadhesive" or "bioadhesive material" means a synthetic material designed to adhere to biological tissues. By definition, bioadhesives are biocompatible materials.

A biocompatible polymer of the invention is built from a single strand of repeating units and up to 5,000 electroactive groups covalently attached to said strand, and it has a molecular weight of up to 3 million Daltons. The crosslinked electroactive groups are derivatives of diazonium, arylsulfonium, diaryliodonium or combinations thereof. Arylsulfonium in present context may refer to mono-, di- or tri-arylsulfonium, for example, triphenylsulfonium, diphenylsulfonium, or alkyldiphenylsulfonium.

The main polymeric strand or backbone can be any bioresorbable polymer that has been FDA-approved as a medical device selected from the group consisting of polyethylene glycol (PEG), PEG fatty acid esters, poly-L-lactic acid (PLLA), poly(lactide-co-glycolide) (PLGA), poly caprolactone (PCL), polyvinyl pyrrolidone (PVP), polyvinyl alcohol (PVA), collagen, chitosan, hydroxy propyl cellulose, polyamides, polyglycerol esters of fatty acids, polysaccharides, polyesters, and combinations thereof. The polysaccharide may be selected from the group consisting of dextran, chitosan, heparin, hyaluronic acid, alginates, starch, glycogen, amylose, amylopectin, cellulose, xylan, and numerous other natural and synthetic polysaccharides.

The specific example of a biocompatible polymer that has been FDA-approved as a medical device is poly(lactic-co-glycolic acid) (PLGA) employed in a form of a thin film matrix. It has been incorporated into a number of drug delivery medical devices due to its numerous advantages, i.e. commercial availability in a range of formulations and controlled release for numerous therapeutics. The PLGA polymer can be blended for independent tailoring of thin film mechanical properties to match soft tissue, controlled drug release, and conductivity.

In a further embodiment, the electroactive diazonium derivative is a compound of the following formula:

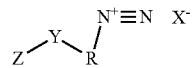

wherein
X is an inorganic or organic anion selected from the group consisting of anion of $F^-$, $Cl^-$, $Br^-$, $I^-$, $BF_4^-$, $BF_3$, $ZnCl_2$, $HSO_4^-$, $PF_6^-$, $HgBr_2$, $HgBr_2Cl_2$, $NO_3^-$, nonafluoro-1-butanesulfonate, trifluoromethanesulfonate, dimethoxy-2-anthracenesulfonate, and methylbenzenesulfonate;
R is a bond or 5-7 membered saturated cyclic or heterocyclic, aromatic or heteroaromatic ring unsubstituted or mono-, di- or tri-substituted with:
$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;
methyl group substituted with 1-3 halogen atoms;
amino group optionally mono or di-substituted with the same or different $C_1$-$C_8$ straight-chain or branched alkyl group;
thiol or thioether group having the same or different $C_1$-$C_8$ straight-chain or branched alkyl group;
sulfone or sulfate group having the same or different $C_1$-$C_8$ straight-chain or branched alkyl group;
nitro, cyano, halogen, hydroxy, carboxylic acid or sulfonic acid group; or
alkoxy or alkoxycarbonyl group having the same or different $C_1$-$C_8$ straight-chain or branched alkyl group;
Y is a bond or saturated and unsaturated $C_1$-$C_{500}$ straight-chain or branched alkyl, alkenyl or alkynyl group, wherein said chain may optionally incorporate at least one hetero atom, and may also comprise at least one substituent; and
Z is any suitable functional group, such as halogen, amino, cyano, hydroxy, aldehyde, alkoxycarbonyl, N-amide, N-hydroxysuccinimide ester, maleimide or thiol.

In specific embodiments, the electroactive diazonium derivative can be selected from the list of:
4-(dimethylamino)-benzene-diazonium salt;
2-chloro-benzene-diazonium salt;
1-naphthalene-diazonium salt;
4-anilino-benzene-diazonium salt;
3,5-dichloro-benzene-diazonium salt;
1-pyrene-diazonium salt;
4-Methoxy-benzene-diazonium salt;
4-bromo-benzene-diazonium salt;
4-formyl-benzene-diazonium salt;
4-Nitro-benzene-diazonium salt;
Fast Red TR salt;
Variamine blue B salt;
4-[ethyl(2-hydroxyethyl)amino]-benzene-diazonium salt;
4-(diethylamino)-2-methyl-benzene-diazonium salt;
4-(ethylamino)-3-methyl-benzene-diazonium salt;
5-chloro-2-methoxy-benzene-diazonium salt;
3-methyl-4-nitro-benzene-diazonium salt;
bis[4-(diethylamino)-2-methyl-benzene-diazonium] salt;
2,4-dichloro-benzene-diazonium salt;
2-methoxy-4-nitro-benzene-diazonium salt;
2-chloro-4-nitro-benzene-diazonium 2-naphthalene-sulfonate;
2,5-diethoxy-4-[(4-methylphenyl)sulfanyl]benzenediazonium salt;
Fast Blue B salt;
9H-fluorene-2-diazonium salt;
9,10-dioxo-9,10-dihydro-1-anthracenediazonium salt; and
2-Methoxy-4-morpholinobenzenediazonium salt.

In a further embodiment, the electroactive diaryliodonium derivative is a compound of the following formula:

Wherein
  X is an inorganic or organic anion selected from the group consisting of anion of F⁻, Cl⁻, Br⁻, I⁻, $BF_4^-$, $BF_3$, $ZnCl_2$, $HSO_4^-$, $PF_6$, $HgBr_2$, $HgBr_2Cl_2$, $NO_3^-$, nonafluoro-1-butanesulfonate, trifluoromethanesulfonate, dimethoxy-2-anthracenesulfonate, and methylbenzenesulfonate;
  Y is a 5-7 membered saturated cyclic or heterocyclic, aromatic or heteroaromatic ring unsubstituted or mono-, di- or tri-substituted with:
  $C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;
  methyl group substituted with 1-3 halogen atoms;
  amino group optionally mono or di-substituted with the same or different $C_1$-$C_8$ straight-chain or branched alkyl group;
  thiol or thioether group having the same or different $C_1$-$C_8$ straight-chain or branched alkyl group;
  sulfone or sulfate group having the same or different $C_1$-$C_8$ straight-chain or branched alkyl group;
  nitro, cyano, halogen, hydroxy, carboxylic acid or sulfonic acid group; or
  alkoxy or alkoxycarbonyl group having the same or different $C_1$-$C_8$ straight-chain or branched alkyl group;
  Z is a 5-7 membered saturated cyclic or heterocyclic, aromatic or heteroaromatic ring unsubstituted or mono-, di- or tri-substituted with:
  $C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;
  methyl group substituted with 1-3 halogen atoms;
  amino group optionally mono or di-substituted with the same or different $C_1$-$C_8$ straight-chain or branched alkyl group;
  thiol or thioether group having the same or different $C_1$-$C_8$ straight-chain or branched alkyl group;
  sulfone or sulfate group having the same or different $C_1$-$C_8$ straight-chain or branched alkyl group;
  nitro, cyano, halogen, hydroxy, carboxylic acid or sulfonic acid group; or
  alkoxy or alkoxycarbonyl group having the same or different $C_1$-$C_8$ straight-chain or branched alkyl group.

In specific embodiments, the electroactive diaryliodonium derivative can be selected from the list of:
  Diphenyliodonium iodide salt;
  bis(4-methoxyphenyl)iodonium salt;
  bis(4-methylphenyl)iodonium salt;
  bis(4-tert-butylphenyl)iodonium salt;
  4-(phenyliodonio)benzoate salt;
  bis(4-fluorophenyl)iodonium salt;
  bis(4-bromophenyl)iodonium salt;
  bis(4-tert-butylphenyl)iodonium salt;
  mesityl(4-methylphenyl)iodonium salt;
  2-(phenyliodonio)benzoate salt;
  2-(phenyliodonio)benzoate;
  (4-nitrophenyl)(phenyl)iodonium;
  phenyl[3-(trifluoromethyl)phenyl]iodonium salt;
  (3-bromophenyl)(mesityl)iodonium salt;
  (2-bromophenyl)(mesityl)iodonium salt;
  mesityl[3-(trifluoromethyl)phenyl]iodonium salt;
  mesityl(4-nitrophenyl)iodonium salt;
  Diphenyleneiodonium salt; and
  3,7-dinitrodibenziodolium salt.

In a further embodiment, the electroactive arylsulfonium derivative is a compound of the following formula:

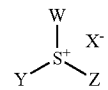

Wherein
  X is an inorganic or organic anion selected from the group consisting of anion of F⁻, Cl⁻, Br⁻, I⁻, $BF_4^-$, $BF_3$, $ZnCl_2$, $HSO_4^-$, $PF_6$, $HgBr_2$, $HgBr_2Cl_2$, $NO_3^-$, nonafluoro-1-butanesulfonate, trifluoromethanesulfonate, dimethoxy-2-anthracenesulfonate, and methylbenzenesulfonate;
  Y is a bond, $C_1$-$C_8$ straight-chain or branched alkyl group, or 5-7 membered saturated cyclic or heterocyclic, aromatic or heteroaromatic ring unsubstituted or mono-, di- or tri-substituted with:
  $C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;
  methyl group substituted with 1-3 halogen atoms;
  amino group optionally mono or di-substituted with the same or different $C_1$-$C_8$ straight-chain or branched alkyl group;
  thiol or thioether group having the same or different $C_1$-$C_8$ straight-chain or branched alkyl group;
  sulfone or sulfate group having the same or different $C_1$-$C_8$ straight-chain or branched alkyl group;
  nitro, cyano, halogen, hydroxy, carboxylic acid or sulfonic acid group; or
  alkoxy or alkoxycarbonyl group having the same or different $C_1$-$C_8$ straight-chain or branched alkyl group;

Z is a bond, $C_1$-$C_8$ straight-chain or branched alkyl group, or 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group;

W is a bond, $C_1$-$C_8$ straight-chain or branched alkyl group, or 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group;

wherein at least two of W, Y and Z are not a bond, $C_1$-$C_8$ straight-chain or branched alkyl group.

In specific embodiments, the electroactive arylsulfonium derivative can be selected from the list of:

Triphenylsulfonium salt;
diphenyl[4-(phenylsulfanyl)phenyl]sulfonium salt;
(4-fluorophenyl)(diphenyl)sulfonium salt;
tris(4-tert-butylphenyl)sulfonium salt;
tris(4-chlorophenyl)sulfonium salt;
(4-chlorophenyl)diphenylsulfonium salt;
tri-p-tolylsulfonium salt;
tris(4-methoxyphenyl)sulfonium salt;
(4-methoxyphenyl)diphenylsulfonium salt;
ethyl(4-methoxyphenyl)(phenyl)sulfonium salt;
(3-chloropropyl)diphenylsulfonium salt; and
(5-chloropentyl)diphenylsulfonium salt.

Reference is now made to FIG. 1 schematically showing synthetic route to the biocompatible polymer crosslinked with diazonium, arylsulfonium, diaryliodonium or combinations thereof.

Figure 2:
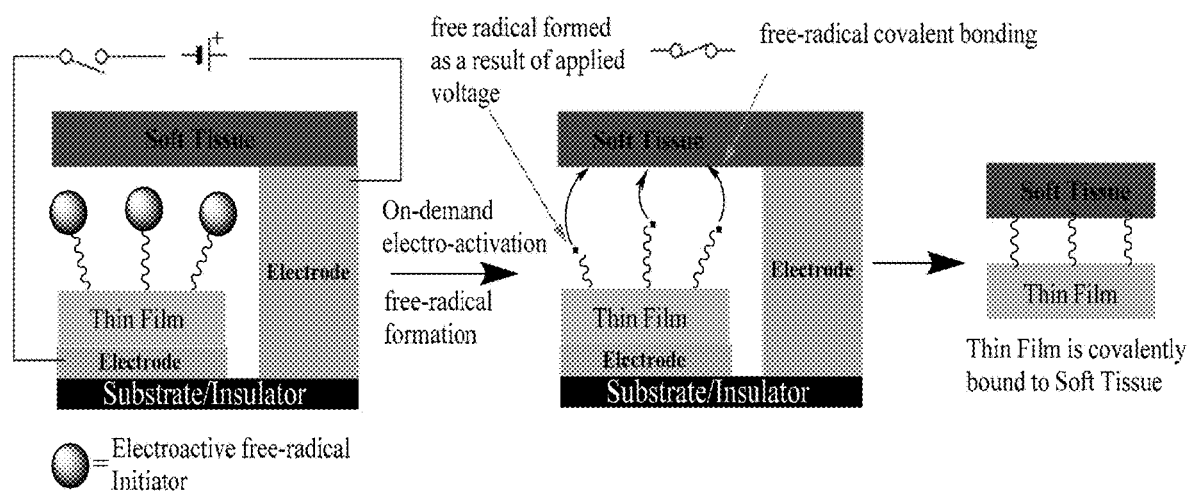
FIG. 2 is a schematic of electroactivated tissue fixation through diazonium, arylsulfonium, or diaryliodonium derivatives surface functionalization.

Reference is now made to FIG. 2 where the biocompatible polymer crosslinked with derivatives of diazonium, arylsulfonium, diaryliodonium or combinations thereof is followed by electro-activation through the electrochemical reduction or oxidation, and soft tissue fixation. Once activated with a voltage potential, for instance at ±5 Volts or by scanning the potential with a fixed or changeable scan rate, free radicals are formed that instantly react and crosslink soft tissues and biomaterials by C—C bond formation.

The novel electroactive polymer used for bioadhesion was conceived after incorporating of key advances in the fields of plasma surface modification, biocompatible polymer functionalized with diazonium, arylsulfonium, diaryliodonium electrochemistry, and antibody-based avidity binding concepts. This polymer allows one to trigger the tissue adhesion in situ, directly at the time and place the tissue fixation is required. The free-radical bond formation employed is advantageous over other known covalent protein bonding methods, as it leaves the bulk protein conformation relatively intact.

Current commercial bioadhesives employ adhesive mechanisms that are relatively inflexible and tend to have narrow applications. The biocompatible polymer of the present invention, based on electro-activation of diazonium, arylsulfonium, or diaryliodonium residues, offers greater flexibility by allowing on-demand activation of the diazonium, arylsulfonium, or diaryliodonium-based surface binding. It is the only electroactivated bioadhesive that is free of monomers and toxic photo-initiators. This electroactive polymer creates a fundamental shift in bioadhesive technology that would have considerable impact on medical implants—in vivo adhesion is a difficult hurdle that has yet to be overcome—especially in wet and protein-filled environments.

Figure 3:
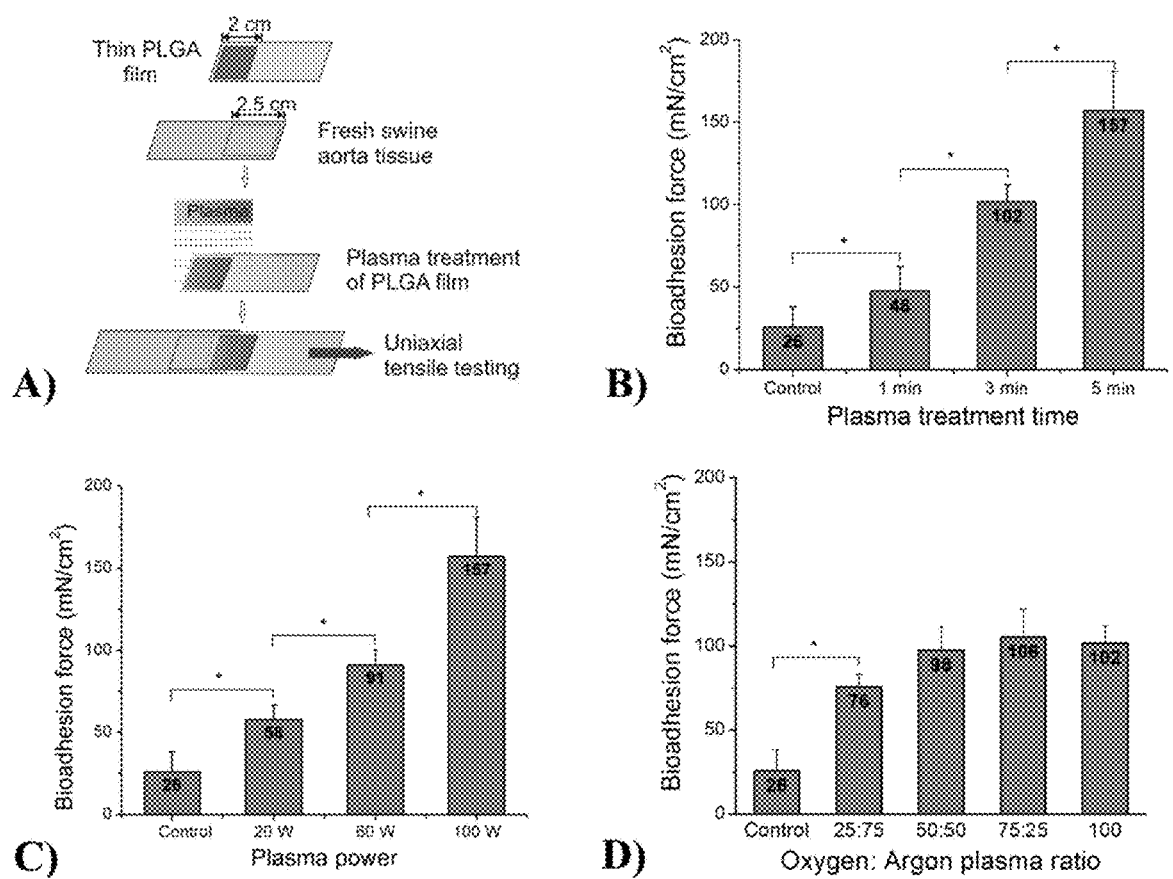
FIG. 3 shows free radicals on surfaces react with nearly any polypeptide chain nearby, instantly creating new covalent bonds. As an example, by applying high surface concentrations of free radicals on PLGA thin films, strong bioadhesion was observed onto soft arterial tissue.

Treatment of surfaces by non-thermal plasmas is well known to create free radicals on biomaterial surfaces while leaving the bulk unaffected. The highly reactive nature of free radicals causes them to have a short half-life, on the order of milliseconds to seconds. However, even within this short life, free radicals react with nearly any polypeptide chains nearby, instantly creating new covalent bonds. As an example, by applying high surface concentrations of free radicals on PLGA thin films, strong bioadhesion was observed onto soft arterial tissue, as seen in FIG. 3.

Free radicals are generally considered detrimental due to their implications in cellular aging. Recently however, several laboratories have revealed that proteins covalently immobilized by free radical mechanisms tend to retain protein conformation and have more functionality. This is a key observation in the design for soft tissue bioadhesives—the higher the protein conformation retained, the lower the local tissue toxicity and inflammation is likely to be.

Although bioadhesives based on free radical covalent bonding are interesting, the plasma generation method is impractical due to the complexity of the plasma ovens and the short term half-lives of the radicals themselves (the majority are likely to be quenched upon atmospheric exposure). In order to take advantage of the free radical covalent bonding, a mechanism is needed to generate the radicals in situ (specifically at the time and place soft tissue bonding is desired). The following unique functional groups—diazonium, arylsulfonium, diaryliodonium—allows in situ formation of free radical by an applied voltage potential.

Reference is now made to FIG. 2, which shows on-demand, electro-activated surface adhesion through surface functionalization of diazonium, arylsulfonium, or diaryliodonium deratives. The surface of PLGA thin films undergo plasma activated ammonia reactions, leaving an amine-functionalized surface that readily reacts with bromine derivatives of diazonium, arylsulfonium, or diaryliodonium compound. Upon an applied voltage potential, the diazonium, arylsulfonium, or diaryliodonium compounds decompose to an extremely reactive free radical. The free radical instantly crosslinks with any nearby polypeptide chains of soft tissues—a fact that has made it widely popular for protein surface functionalization.

The electroactive functional groups allow in situ free radical generation with little to no toxic byproducts for relatively harmless protein backbone covalent bonding. Many other event activated free radical forming are available, i.e. photoactive compounds such as azides, diazo compounds, benzophenone, anthraquinone, diaryl diazomethanes, and psoralene. However, the UV irradiation is required for photoactivation—the large intensities of ionizing radiation required for photo-activation can cause harm to the adjacent tissues.

The electroactive mechanism of adhesion has many advantages over other adhesion mechanisms. For example, cyanoacrylate cannot be activated on demand, often begins to polymerize at the slightest amount of moisture, and tends to be toxic after degradation. Light activated acrylate or epoxide polymerization based bioadhesives tend to have high front temperatures (causing thermal damage) and leave behind toxic monomers by-products, as well as photoinitiators. The diazonium functional group leaves no monomer or photoinitiator by-products after curing.

With the use of commercially available diazonium and diaryliodonium derivatives, novel poly-diazoniums and poly-diaryliodoniums can be easily synthesized by employing antibody inspired avidity-type binding mechanisms in a one-pot synthesis.

"Avidity" is a term to define the combined strength of multiple bonding interactions simultaneously with one or more targets. Poly-diazoniums and poly-diaryliodoniums bioadhesion attempts to avidity bond soft tissue to soft tissue or soft tissue to other relevant biomaterials. The poly-diazonium and poly-diaryliodonium based bioadhesive could be tailored via numerous methods, depending on the application. For example, interfacial bioadhesion strength could be adjusted by varying the density of the functional groups on the polymer backbone or by controlling the intensity/time of the applied voltage potential, so only the needed fraction of diazonium or diaryliodoniums are activated into free-radicals.

In light of the above, the biocompatible polymer of the invention has the following advantages over commercially available bioadhesives, such as cyanoacrylates and fibrin-based bioadhesives:

Can stick to wet or dry materials;
Activated on demand with immediate electro-curing;
Adapted to existing biomaterials that have been FDA-approved as a medical device;
Adhesion mechanism leaves protein in tissues relatively intact;
Avoids any toxic photoinitiators;
Degradation has no toxic by-products; and
Multiple functional groups can be easily converted in the reactive diazonium, triarylsulfonium, alkyldiphenylsulfonium, or diaryliodonium derivatives, including primary and secondary amines, ketones, and aldehydes.

The electroactive bioadhesive composition may further comprise the electroactive polymer of the present invention and suitable solvents, surfactants, stabilizers, fillers and other additives. The additives may be anti-inflammatory drugs, anti-proteases, antibiotics, and/or anti-restenosis compounds. The composition can be in a form of hydrogel, biocompatible film, patch or bandage.

Bioadhesive hydrogels could have multiple uses in surgeries, particularly in anastomosis procedures, where two tubes or lumens must be joined. For example, gastrointestinal surgeries towards cancer removal, obesity treatments, and bowel obstructions. Blood vessel anastomosis is in significant need of new bioadhesives. Sutures currently limit blood vessel anastomosis to vessels of more than 1 mm in diameter, which limits reattachment of amputated limbs.

The bioadhesive hydrogels can be prepared from many common biocompatible polymers and polyglycans, for example dextran, chitosan, heparin, hyaluronic acid, alginates, starch, glycogen, amylose, amylopectin, cellulose, xylan, and numerous other natural and synthetic polysaccharides. Polysaccharides can be functionalized with diazonium, arylsulfonium, or diaryliodonium derivatives through primary and secondary amines groups, carbonyl groups such as aldehyde groups, ketones, and carboxylic acids. Most preferably are the primary amines and aldehyde groups. Most polysaccharides can be turned into poly-aldehydes through oxidation reactions such as treatment with sodium periodate, treatment with nitrous acid, etc.

Bioadhesive thin films have numerous applications across the medical spectrum. Biodegradable thin films of the present invention offer a more cost effective replacement for sutures, band aids, or dressings. Drug impregnated with diazonium, arylsulfonium, or diaryliodonium derivatives-based bioadhesives offer local drug delivery to a variety of soft-tissues, thereby eliminating systemic drug side effects and first-pass liver metabolism, while allowing delivery of acid-labile therapeutics (which cannot be taken orally). The novel approach inherent in the diazonium, arylsulfonium, diaryliodonium derivatives-based bioadhesive design allows adhesion even in wet, protein filled environments—a claim no other bioadhesive has yet to make. This allows targeting of the vasculature ailments by piggybacking the bioadhesive thin films of the invention on modified angioplasty balloon catheters.

In addition, the composition can be in a form of hydrogel, biocompatible film, patch or bondage. In addition, the composition may contain conductive particles or polymers of size less than 50 micron made of gold, iron, iron oxides, platinum, magnesium, graphene, carbon black, carbon nanotubes, polyacetylene, poly(3-alkyl-thiophene), polyaniline, polyisothianaphthalene, poly-(p-phenylene), poly-(p-phenylene vinylene), polypyrole, polythiophene, or combinations thereof. The composition is electrically conductive with conductivity greater than 0.01 siemen per centimeter.

In additional embodiment, the conductive particles can be coated with anionic or cationic coating comprising fatty acids, silica, polyethylene glycol, pluronics, poloxamers, polydopamine, polylysine or any suitable peptide.

Bioadhesives towards organ sealants or vascular tissues is the preferable application, due to the plethora of sealants needed, ease of reach with common catheters, or both (sealants for air/lung or dura mater/fluid leakages, trauma haemostasis, or intestinal anastomoses).

According to the embodiments of the invention, the composition may be used in surgery, such as gastrointestinal surgery towards cancer removal, anastomoses procedures, such as blood vessel anastomoses wherein two tubes or lumens must be joined, tissue fixation, suture sealing and replacement, treatment of lung punctures, body lumen punctures or leaks, cerebrospinal fluid membrane damages, obesity treatments, and bowel obstructions.

A method for the preparation of the electroactive polymer of the present invention involves the following steps:
(a) Preparing a solution of said biocompatible polymer having concentration of 0.1 to 100 mg/ml at pH 7.2;
(b) Dissolving said diazonium, arylsulfonium, or diaryliodonium derivative compound in a suitable organic solvent within the concentration range of 0.01 to 100 mM;
(c) Mixing and reacting the solution of said biocompatible polymer prepared in a) with the solution of the derivative prepared in b), in order to covalently attach the derivatives groups to the polymer strand; that is in the form of a thin film on a conductive material, i.e. the electrode.
(d) Purifying said polymer modified in c) on a Sephadex G-25 column or using other conventional purification and separation techniques in order to remove the unbound derivative molecules.

According to another embodiment of the invention, method of tissue fixation comprises the following steps:
(a) Applying the electroactive bioadhesive composition of the present invention, being a hydrogel, film, patch or bondage, to a tissue to be fixed; and
(b) Applying a voltage potential to an electrode on which the electroactive polymer is placed, across the composition and tissue area with negative 10 to positive 10 Volts vs. a reference electrode that can be of any type such as Ag/AgCl or Ag wire or any other electrode that has a constant potential, which depends on the composition, in an electrolyte having a concentration of between 0.01 and 1 M.

The applied potential voltage range of the electro-activation is between negative 10 Volts and positive 10 Volts, preferably between negative 5 and positive 5 Volts, and most preferably negative 2 Volts and positive 2 Volts and time of potential voltage in both cases is less than 20 minutes. The application of potential can be in the form of a constant or variable potential including AC.

Although portions of the discussion herein may relate to bioadhesion, the present invention is not limited in this regard, and may include, for example, additional surgical procedures.

A biocompatible polymer, composition and methods in accordance with some embodiments of the invention may be used, for example, in conjunction with a device which may be inserted into a human body. However, the scope of the present invention is not limited in this regard. For example, some embodiments of the invention may be used in conjunction with a device which may be inserted into a non-human body or an animal body.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An electroactive bioadhesive composition comprising an electroactive biocompatible polymer comprising a biocompatible polymer;
wherein the biocompatible polymer comprises a single strand of repeating units and up to 5,000 electroactive groups covalently attached to said strand, wherein precursors of said electroactive groups are selected from the group consisting of a diazonium derivative, an arylsulfonium derivative, a diaryliodonium derivative, and combinations thereof;
wherein the biocompatible polymer is selected from the group consisting of poly-L-lactic acid (PLLA), poly (lactide-co-glycolide) (PLGA), poly caprolactone (PCL), polyvinyl pyrrolidone (PVP), polyvinyl alcohol (PVA), collagen, hydroxy propyl cellulose, polyglycerol esters of fatty acids, polysaccharides, and combinations thereof.

2. The electroactive bioadhesive composition according to claim 1 further comprising additives, wherein said additives are anti-inflammatory drugs, anti-proteases, antibiotics, or anti-restenosis compounds.

3. The electroactive bioadhesive composition according to claim 1, wherein said composition is in a form of a hydrogel.

4. The electroactive bioadhesive composition according to claim 1, wherein said composition is in a form of a biocompatible film, a patch or a bondage.

5. The electroactive bioadhesive composition according to claim 1, further comprising conductive particles having a size of less than 50 micron, wherein the conductive particles comprise gold, iron, iron oxides, platinum, magnesium, graphene, carbon black, carbon nanotubes, polyacetylene, poly(3-alkyl-thiophene), polyaniline, polyisothianaphthalene, poly-(p-phenylene), poly-(p-phenylene vinylene), polypyrrole, polythiophene, or combinations thereof.

6. The electroactive bioadhesive composition according to claim 5, wherein said electroactive bioadhesive composition is electrically conductive with a conductivity greater than 0.01 siemen per centimeter.

7. The composition according to claim 5, wherein the conductive particles are coated with an anionic or a cationic coating comprising fatty acids, polydopamine, polylysine or a peptide.

8. The composition according to claim 5, wherein said conductive particles are coated with an anionic or a cationic coating.

9. A method for the preparation of electroactive biocompatible polymer of claim 1, comprising the steps of:
(a) preparing a solution of said biocompatible polymer having a concentration of 0.1 to 100 mg/ml at pH 7.2;
(b) dissolving said diazonium derivative, arylsulfonium derivative, diaryliodonium derivative, or combinations thereof, in an organic solvent within the concentration range of 0.01 to 100 mM;
(c) mixing and reacting the solution of said biocompatible polymer prepared in a) with the solution of the derivative prepared in b), in order to covalently attach the derivative to the biocompatible polymer; and
(d) purifying said biocompatible polymer modified in c) using conventional purification and separation techniques in order to remove unbound derivative molecules.

10. A method of tissue fixation comprising the steps of:
(a) applying the electroactive bioadhesive composition of claim 1 to a tissue to be fixed;
(b) contacting an electrode with the electroactive biocompatible composition and contacting another electrode with the tissue to be fixed, followed by
(c) applying a voltage potential to the electrode contacting the electroactive biocompatible composition, across the electroactive biocompatible composition and tissue area with negative 10 to positive 10 Volts vs. an Ag/AgCl or Ag wire or any other electrode that has a constant potential.

11. The method according to claim 10, wherein the voltage potential applied is between negative 10 and positive 10 Volts.

12. The method according to claim 10, wherein the application of voltage potential is in the form of a constant or variable potential including AC.

13. The method according to claim 10, wherein a time of applied voltage is less than 20 minutes.

* * * * *